United States Patent [19]

Hsu

[11] Patent Number: 5,041,457
[45] Date of Patent: Aug. 20, 1991

[54] SYNERGISTIC MICROBICIDAL COMBINATIONS CONTAINING 2-N-OCTYL-3-ISOTHIAZOLONE AND CERTAIN COMMERCIAL BIOCIDES

[75] Inventor: Jemin C. Hsu, Fort Washington, Pa.

[73] Assignee: Rohm and Haas Company, Philadelphia, Pa.

[21] Appl. No.: 539,254

[22] Filed: Jun. 18, 1990

Related U.S. Application Data

[62] Division of Ser. No. 322,455, Mar. 10, 1989, Pat. No. 4,964,892.

[51] Int. Cl.$^5$ ............................................. A01N 43/80
[52] U.S. Cl. .................................... 514/372; 514/389; 71/67
[58] Field of Search ..................... 71/67; 514/372, 389; 548/308, 213

[56] References Cited

U.S. PATENT DOCUMENTS 3,717,579  2/1973  Hofmann ............................. 252/106
3,761,488  9/1973  Lewis et al. ......................... 548/213
3,987,184  10/1976 Foelsch ................................ 514/389
4,105,431  8/1978  Lewis et al. ........................... 71/67
4,172,140  10/1979 Shull et al. .......................... 514/389
4,173,643  11/1979 Law ...................................... 424/270
4,252,694  2/1981  Lewis et al. ......................... 252/545
4,265,899  5/1981  Lewis et al. ......................... 252/106
4,279,762  7/1981  Lewis et al. ......................... 252/475
4,279,796  7/1981  Lewis et al. ......................... 524/316
4,906,651  3/1990  Hsu ...................................... 514/372

FOREIGN PATENT DOCUMENTS 2201595  9/1988  United Kingdom .

Primary Examiner—Allen J. Robinson
Assistant Examiner—John D. Pak
Attorney, Agent, or Firm—Michael B. Fein

[57] ABSTRACT

Synergistic antimicrobial and biocidal compositions comprising 2-n-octyl-4-isothizolin-3-one and one or more known biocides for more effective, and broader control of miccroorganisms in various industrial systems are disclosed.

5 Claims, No Drawings

1

SYNERGISTIC MICROBICIDAL COMBINATIONS CONTAINING 2-N-OCTYL-3-ISOTHIAZOLONE AND CERTAIN COMMERCIAL BIOCIDES

This is a divisional of application Ser. No. 322,455, filed Mar. 10, 1989, now U.S. Pat. No. 4,964,892.

BACKGROUND OF THE INVENTION

1. Field of the Invention

This invention relates to synergistic antimicrobial or biocidal compositions including an isothiazolone and one or more of known biocides for more effective and broader control of micro-organisms in various industrial systems and for household products, agricultural products, and biomedical products, etc. In particular, the present invention relates to the use of a composition of 2-n-octyl-4-isothiazolin-3-one (also known as 2-n-octyl-3-isothiazolone or 2-n-octylisothiazolone) with one or more of the following 21 compounds: 2-(hydroxymethyl)amino-2-methylpropanol; 2-(hydroxymethyl)aminoethanol; 5-bromo-5-nitro-1,3-dioxane; hexahydro-1,3,5-triethyl-s-triazine; α-benzoyl-α-chloroformaldoxime; benzylbromoacetate; p-chloro-m-xylenol; bis-(2-hydroxy-5-chlorophenyl)sulfide; p-tolyldiiodomethylsulfone; 3-iodo-2-propynylbutylcarbamate; 5-hydroxypoly(methyleneoxy)-methyl-1-aza-3,7-dioxabicyclo(3,3,0)octane; dipropylamine ether; dodecylamine; N-(hydroxymethyl)-N'-(1,3-di(hydroxymethyl)-2,5-dioxo-4-imidazolidinyl)-N'-(hydroxymethyl)urea; 1-(3-chloroallyl)-3,5,7-triaza-1-azoniaadamantane chloride; 1,2-dibromo-2,4-dicyanobutane; N,N-dimethyl-N'-phenyl-N'-(fluorodichloromethylthio)sulfamide; N,N'-di(-hydroxmethyl)-5,5'-dimethylhydantoin; 2-bromo-2-nitropropanediol; methylene-bis-thiocyanate; and 2,4-dichlorobenzyl alcohol.

2. Prior Art

The isothiazolones are described in U.S. Pat. Nos. 3,761,488; 4,105,431; 4,252,694; 4,265,899 and 4,279,762, and elsewhere. The 2-n-octyl-4-isothiazolin-3-one (octhilinone) is a superior fungicide with relatively lower activity against Gram-negative bacteria. The low activity against Gram negative bacteria has limited its uses in industrial systems where both bacteria and fungi are fouling the systems. To control these situations requires a higher concentration of octhilinone, which increases the cost of the treatment. Therefore, it is useful to find compositions which are more effective and exert broader control.

It has been discovered that compositions formed from 2-n-octyl-4-isothiazolin-3-one and one or more of the 21 specified compounds (supra) within specified range of ratios unexpectedly afforded synergistic antimicrobial activity against a wide range of microorganisms. The synergy in which the disruptive action on the organisms by the two compounds together is greater than the sum of both compounds taken alone does not arise from the expected activity of the components or from the expected improvement in activity. As a result of the synergy, the effective dose which can be lowered is not only more economical but also increases safety margin. The synergistic compositions provide more effective and broader control of microorganisms in a number of industrial systems.

It is the principal object of this invention to provide the use of synergistic compositions which overcome the disadvantages of the known biocidal compositions.

Important applications of the synergistic antimicrobial compositions of the present invention include but are not limited to: inhibiting the growth of bacteria and fungi in aqueous paints and coatings, adhesives, sealants, latex emulsions, and joint cements; preserving wood; preserving cutting fluids, controlling slime-producing bacteria and fungi in pulp and papermills and cooling towers; as a spray or dip treatment for textiles and leather to prevent mold growth; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; preserving fuel; controlling microorganisms contamination and deposits in oil field drilling fluids and muds, and in secondary petroleum recovery processes; preventing bacterial and fungal growth in paper coatings and coating processes; controlling bacterial and fungal growth and deposits during the manufacture of various specialty boards, e.g., carboard and particle board; preventing sap stain discoloroation on freshly cut wood of various kinds; controlling bacterial and fungal growth in clay and pigment slurries of various types; as a hard surface disinfectant to prevent growth of bacteria and fungi on walls, floors, etc.; as a preservative for cosmetic and toiletry raw materials, floor polishes, fabric softeners, household and industrial cleaners; in swimming pools to prevent algae growth; inhibiting the growth of harmful bacteria, yeasts, fungi on plants, trees, fruits, seeds, or soil; preserving agricultural formulations, electrodeposition systems, diagnostic and reagent products, medical devices; protecting animal dip compositions against the buildup of microorganisms, and in photoprocessing to prevent buildup of microorganisms, and the like.

The synergistic compositions of the invention may be added separately to an industrial system or may be formulated as a simple mixture comprising its essential ingredients, and if desired a suitable carrier or solvent, or as an aqueous emulsion or dispersion.

SUMMARY OF THE INVENTION

Compositions of octhilinone and one or more of the following compounds when employed at specified range of ratios exhibit synergistic biocidal and antimicrobial activity against a wide range of microorganisms: 2-(hydroxymethyl)amino-2-methylpropanol; 2-(hydroxymethyl) aminoethanol; 5-bromo-5-nitro-1,3-dioxane; hexahydro-1,3,5-triethyl-s-triazine; α-benzoyl-α-chloroformaldoxime; benzylbromoacetate; p-chloro-m-xylenol; bis-(2-hydroxy-5-chlorophenyl)sulfide; p-tolyldiiodomethylsulfone; 3-iodo-2-propynylbutylcarbamate; 5-hydroxypoly(methyleneoxy)-methyl-1-aza-3,7-dioxabicyclo(3,3,0)octane; dipropylamine ether; dodecylamine; N-(hydroxymethyl)-N'-(1,3-di(hydroxymethyl)-2,5-dioxo-4-imidazolidinyl)-N'-(hydroxymethyl)urea; 1-(3-chloroallyl)-3,5,7-triaza-1-azoniaadamantane chloride; 1,2-dibromo-2,4-dicyanobutane; N,N-dimethyl-N'-phenyl-N'-(fluorodichloromethylthio)sulfamide; N,N'-di(hydroxymethyl)-5,5-dimethylhydantoin; 2-bromo-2-nitropropanediol; methylene-bis-thiocyanate; and 2,4-dichlorobenzyl alcohol.

GENERAL DESCRIPTION OF THE PREFERRED EMBODIMENT

The invention also relates to a method of inhibiting the growth of bacteria, fungi or algae in a locus subject to contamination by bacteria, fungi or algae, which comprises incorporating into or onto the locus in an amount which is effective to adversely affect the growth of bacteria, fungi or algae one or more of the synergistic combinations described above.

The composition of the invention can be formulated as a solution in water. While the amount of the instant composition in the formulated solution can vary over a wide range, the solutions can conveniently be formulated to contain from about 20 to about 400 ppm of the composition in solution, with the preferred range being from about 25 to 200 ppm of the composition. In formulating the solutions, other solvents which are water-miscible, such as ethyl alcohol, propyl alcohol, isopropyl alcohol, diethylene glycol, dipropylene glycol, polyethylene glycol, diethylene glycol, ethyl ether, and the like, may be employed in order to aid in solubilizing the active components. Furthermore, various other conventional additives may be employed, such as surfactants, dispersing agents, corrosion inhibitors, and the like.

In general, the ratio of the first component to second component is in the range of from about 150:1 to about 1:400. The other specific and preferred ratios are given in the examples.

The synergism of these two-components compositions is demonstrated by testing a wide range of concentrations and ratios of compounds, generated by two-fold serial dilutions in a liquid growth medium of a biocide in one dimension and another biocide in the second dimension, against a bacterium Escherichia coli (ATCC 11229) or a fungus Candida albicans (ATCC 11651), or a mixed culture of bacteria and fungi which are natural contaminants of a metalworking fluid. Each test tube was inoculated to about $2 \times 10^7$ bacteria per ml or $2 \times 10^6$ fungi per ml. The lowest concentrations of each compound or mixtures to inhibit visible growth (turbidity) at 37° for E. coli and at 30° C. for C. albicans, or the mixed culture for over 2 days is the minimum inhibitory concentration (MIC). The lowest concentration of each compound or the mixtures to kill 99.99% of fungi or 99.999% of bacteria after certain period of exposure from 1 day to 7 days is taken as minimum biocidal concentration (MBC). Both MIC and MBC are taken as end points of activity. End points for the mixtures of compound A and compound B were then compared with the end points for compound A alone and compound B alone. Synergism was determined by a commonly used and accepted method described by Kull, F. C.; Eisman, P. C.; Sylwestrowicz, H. D. and Mayer, R. L., in applied Microbiology 9:538–541 (1961) using the ratio determined by $$Qa/QA + Qb/QB = \text{Synergy Index (SI)}$$

wherein

QA = concentration of compound A in parts per million (ppm), acting alone, which produced an end point.
Qa = concentration of compound A in ppm, in the mixture, which produced an end point.
QB = concentration of compound B in ppm, acting alone, which produced an end point.
Qb = concentration of compound B in ppm, in the mixture, which produced an end point when the sum of Qa/QA and Qb/QB is greater than one, antagonism is indicated. When the sum is equal to one additivity is indicated, and when less than one synergism is demonstrated.

The test results for demonstration of synergism of biocide combinations are shown in Table 1 through Table 21. Each table is organized to show:
1. the specific combination of compound A and compound B;
2. test against E. coli or C. albicans, or a mixed culture of bacteria and fungi;
3. test medium by either trypticase soy broth (TSB) or a minimal salt medium +0.2% glucose (M9G);
4. the method of evaluation by either MIC or MBC. The MBCld means MBC determined after 1-day exposure to biocides. MBC2d means MBC determined after 2-days exposure to biocides, etc.;
5. the end-point activity in ppm measured by MIC or MBC for compound A alone (QA), for compound B alone (QB), for compound A in the mixture (Qa), or for compound B in the mixture (Qb);
6. the calculation for synergy index (SI) based on the formula SI = Qa/QA + Qb/QB, and for the ratio of compound A to compound B in the synergistic combinations (Qa:Qb);
7. the range of ratios for synergism and the preferred ratios.

TABLE 1

| | Combination of Octhilinone and 2-(Hydroxymethyl)amino-2-methylpropanol | | | | | | | |
|---|---|---|---|---|---|---|---|---|
| Method of evaluation | end-point activity in ppm | | | | calculations | | | |
| | QA | QB | Qa | Qb | Qa/QA | Qb/QB | SI | Qa:Qb |
| | test against C. albicans in TSB medium | | | | | | | |
| MIC | 2.5 | 1000.0 | 1.3 | 500.0 | 0.50 | 0.50 | 1.00 | 1:400 |
| | test against E. coli in M9G medium | | | | | | | |
| MIC | 125.0 | 62.0 | 2.0 | 31.0 | 0.02 | 0.50 | 0.52 | 1:16 |
| | 125.0 | 62.0 | 8.0 | 16.0 | 0.06 | 0.26 | 0.32 | 1:2 |
| | 125.0 | 62.0 | 62.0 | 8.0 | 0.50 | 0.13 | 0.63 | 8:1 |
| MBCld | 250.0 | 250.0 | 16.0 | 31.0 | 0.06 | 0.12 | 0.19 | 1:2 |
| | 250.0 | 250.0 | 31.0 | 16.0 | 0.12 | 0.06 | 0.19 | 2:1 |
| | 250.0 | 250.0 | 62.0 | 8.0 | 0.25 | 0.03 | 0.28 | 8:1 |
| MBC4d | 125.0 | 62.0 | 2.0 | 31.0 | 0.02 | 0.50 | 0.52 | 1:16 |
| | 125.0 | 62.0 | 8.0 | 16.0 | 0.06 | 0.26 | 0.32 | 1:2 |
| | 125.0 | 62.0 | 62.0 | 8.0 | 0.50 | 0.13 | 0.63 | 8:1 |
| MBC7d | 125.0 | 62.0 | 2.0 | 31.0 | 0.02 | 0.50 | 0.52 | 1:16 |

TABLE 1-continued

Combination of Octhilinone and 2-(Hydroxymethyl)amino-2-methylpropanol

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| | 125.0 | 62.0 | 8.0 | 16.0 | 0.06 | 0.26 | 0.32 | 1:2 |

Compound A = Octhilinone
Compound B = 2-(Hydroxymethyl)amino-2-methylpropanol
The synergistic ratios of compound A:compound B range from 8:1 to 1:16.
The preferred ratios are 1:2 to 1:16.

TABLE 2

Combination of Octhilinone and 2-(Hydroxymethyl)aminoethanol

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| | test against *E. coli* in M9G medium | | | | | | | |
| MIC | 125.0 | 62.0 | 4.0 | 31.0 | 0.03 | 0.50 | 0.53 | 1:8 |
| | 125.0 | 62.0 | 62.0 | 8.0 | 0.50 | 0.13 | 0.63 | 8:1 |
| MBC1d | 250.0 | 500.0 | 62.0 | 16.0 | 0.25 | 0.03 | 0.28 | 4:1 |
| MBC4d | 125.0 | 62.0 | 4.0 | 31.0 | 0.03 | 0.50 | 0.53 | 1:8 |
| | 125.0 | 62.0 | 62.0 | 8.0 | 0.50 | 0.13 | 0.63 | 8:1 |
| MBC7d | 125.0 | 62.0 | 4.0 | 31.0 | 0.03 | 0.50 | 0.53 | 1:8 |
| | 125.0 | 62.0 | 62.0 | 8.0 | 0.50 | 0.13 | 0.63 | 8:1 |
| | test against *C. albicans* in TSB medium | | | | | | | |
| MIC | 1.3 | 1000.0 | 0.6 | 31.0 | 0.50 | 0.03 | 0.53 | 1:50 |
| MBC1d | 1.3 | 1000.0 | 0.6 | 125.0 | 0.50 | 0.13 | 0.63 | 1:200 |
| MBC4d | 1.3 | 1000.0 | 0.6 | 125.0 | 0.50 | 0.13 | 0.63 | 1:200 |

Compound A = Octhilinone
Compound B = 2-(Hydroxymethyl)aminoethanol
The synergistic ratios of compound A:compound B range from 8:1 to 1:200.
The preferred ratios are 1:8 to 8:1

TABLE 3

Combination of Octhilinone and 5-Bromo-5-nitro-1,3-dioxane

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| | test against *E. coli* in TSB medium | | | | | | | |
| MBC | 125.0 | 50.0 | 16.0 | 25.0 | 0.13 | 0.50 | 0.63 | 1:1.6 |
| MBC | 125.0 | 50.0 | 2.0 | 25.0 | 0.02 | 0.50 | 0.52 | 1:1.25 |
| | test against *C. albicans* in TSB medium | | | | | | | |
| MIC | 2.0 | 25.0 | 0.5 | 3.1 | 0.25 | 0.12 | 0.37 | 1:6.2 |
| | 2.0 | 25.0 | 1.0 | 0.1 | 0.50 | 0.00 | 0.50 | 10:1 |
| MBC2d | 2.0 | 25.0 | 1.0 | 0.4 | 0.50 | 0.02 | 0.52 | 25:1 |
| MBC6d | 2.0 | 25.0 | 1.0 | 0.8 | 0.50 | 0.03 | 0.53 | 1.2:1 |
| | test against *E. coli* in M9G medium | | | | | | | |
| MIC | 125.0 | 10.0 | 62.0 | 0.6 | 0.50 | 0.06 | 0.56 | 100:1 |
| | 125.0 | 10.0 | 16.0 | 2.5 | 0.13 | 0.25 | 0.38 | 6.4:1 |
| | 125.0 | 10.0 | 2.0 | 5.0 | 0.02 | 0.50 | 0.52 | 1:2.5 |
| MBC1d | 125.0 | 20.0 | 62.0 | 0.6 | 0.50 | 0.03 | 0.53 | 100:1 |
| | 125.0 | 20.0 | 31.0 | 2.5 | 0.25 | 0.13 | 0.37 | 12.5:1 |
| | 125.0 | 20.0 | 8.0 | 5.0 | 0.06 | 0.25 | 0.31 | 1.5:1 |
| | test against a mixed-culture in TSB medium | | | | | | | |
| MIC | 250.0 | 12.5 | 8.0 | 5.0 | 0.03 | 0.40 | 0.43 | 1.5:1 |
| MBC1d | 250.0 | 50.0 | 31.0 | 20.0 | 0.12 | 0.40 | 0.52 | 1.5:1 |
| MBC2d | 250.0 | 50.0 | 31.0 | 20.0 | 0.12 | 0.40 | 0.52 | 1.5:1 |
| MBC6d | 250.0 | 12.5 | 8.0 | 5.0 | 0.03 | 0.40 | 0.43 | 1.5:1 |

Compound A = Octhilinone
Compound B = 5-Bromo-5-nitro-1,3-dioxane
The synergistic ratios of compound A:compound B range from 100:1 to 1:12.5.
The preferred ratios are 1.5:1 to 1:12.5.

TABLE 4

Combination of Octhilinone and Hexahydro-1,3,5-triethyl-s-triazine

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| | test against *E. coli* in M9G | | | | | | | |
| MIC | 125.0 | 16.0 | 62.0 | 4.0 | 0.50 | 0.25 | 0.75 | 16:1 |
| MBC1d | 250.0 | 125.0 | 62.0 | 16.0 | 0.25 | 0.13 | 0.38 | 4:1 |
| MBC4d | 125.0 | 16.0 | 62.0 | 4.0 | 0.50 | 0.25 | 0.75 | 16:1 |
| MBC7d | 125.0 | 16.0 | 62.0 | 4.0 | 0.50 | 0.25 | 0.75 | 16:1 |

Compound A = Octhilinone
Compound B = Hexahydro-1,3,5-triethyl-s-triazine
The synergistic ratios of compound A:compound B range from 4:1 to 16:1.
The preferred ratios are 4:1 to 16:1.

TABLE 5

Combination of Octhilinone and α-Benzoyl-α-chloroformaldoxime

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| *test against E. coli in M9G medium* | | | | | | | | |
| MIC | 125.0 | 500.0 | 8.0 | 125.0 | 0.06 | 0.25 | 0.31 | 1:15 |
| | 125.0 | 500.0 | 31.0 | 62.0 | 0.25 | 0.12 | 0.37 | 1:2 |
| | 125.0 | 500.0 | 62.0 | 31.0 | 0.50 | 0.06 | 0.56 | 2:1 |
| MBCId | 250.0 | 500.0 | 4.0 | 250.0 | 0.02 | 0.50 | 0.52 | 1:62 |
| | 250.0 | 500.0 | 62.0 | 62.0 | 0.25 | 0.12 | 0.37 | 1:1 |
| | 250.0 | 500.0 | 125.0 | 2.0 | 0.50 | 0.00 | 0.50 | 62:1 |
| MBC4d | 125.0 | 500.0 | 8.0 | 125.0 | 0.06 | 0.25 | 0.31 | 1:15 |
| | 125.0 | 500.0 | 31.0 | 62.0 | 0.25 | 0.12 | 0.37 | 1:2 |
| | 125.0 | 500.0 | 62.0 | 31.0 | 0.50 | 0.06 | 0.56 | 2:1 |
| MBC7d | 125.0 | 500.0 | 8.0 | 125.0 | 0.06 | 0.25 | 0.31 | 1:15 |
| | 125.0 | 500.0 | 31.0 | 62.0 | 0.25 | 0.12 | 0.37 | 1:2 |
| | 125.0 | 500.0 | 62.0 | 31.0 | 0.50 | 0.06 | 0.56 | 2:1 |
| *test against C. albicans in TSB medium* | | | | | | | | |
| MIC | 1.0 | 2000.0 | 0.3 | 31.0 | 0.25 | 0.02 | 0.27 | 1:100 |
| MBC2d | 2.0 | 2000.0 | 0.3 | 31.0 | 0.13 | 0.02 | 0.15 | 1:100 |
| MBC6d | 1.0 | 2000.0 | 0.3 | 31.0 | 0.25 | 0.02 | 0.27 | 1:100 |
| *test against E. coli in TSB medium* | | | | | | | | |
| MIC | 250.0 | 2000.0 | 125.0 | 62.0 | 0.50 | 0.03 | 0.53 | 2:1 |
| MBC2d | 250.0 | 2000.0 | 125.0 | 62.0 | 0.50 | 0.03 | 0.53 | 2:1 |
| MBC6d | 250.0 | 2000.0 | 125.0 | 62.0 | 0.50 | 0.03 | 0.53 | 2:1 |

Compound A = Octhilinone
Compound B = α-Benzoyl-α-chloroformaldoxime
The synergistic ratios of compound A:compound B range from 62:1 to 1:100.
The preferred ratios are 2:1 to 1:2.

TABLE 6

Combination of Octhilinone and Benzylbromoacetate

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| *test against C. albicans in TSB medium* | | | | | | | | |
| MIC | 2.5 | 12.5 | 0.1 | 3.1 | 0.03 | 0.25 | 0.28 | 1:40 |
| | 2.5 | 12.5 | 0.3 | 1.6 | 0.12 | 0.13 | 0.25 | 1:5 |
| *test against a mixed culture in TSB medium* | | | | | | | | |
| MIC | 250.0 | 100.0 | 62.0 | 50.0 | 0.25 | 0.50 | 0.75 | 1.2:1 |
| MBC2d | 250.0 | 200.0 | 62.0 | 50.0 | 0.25 | 0.25 | 0.50 | 1.2:1 |
| MBC6d | 250.0 | 200.0 | 62.0 | 50.0 | 0.25 | 0.25 | 0.50 | 1.2:1 |
| *test against E. coli in M9G medium* | | | | | | | | |
| MIC | 125.0 | 12.5 | 31.0 | 1.6 | 0.25 | 0.13 | 0.38 | 20:1 |
| | 125.0 | 12.5 | 16.0 | 3.1 | 0.13 | 0.25 | 0.38 | 5:1 |
| MBCId | 125.0 | 25.0 | 62.0 | 1.6 | 0.50 | 0.06 | 0.56 | 40:1 |
| | 125.0 | 25.0 | 31.0 | 3.1 | 0.25 | 0.12 | 0.37 | 10:1 |
| | 125.0 | 25.0 | 16.0 | 12.5 | 0.13 | 0.50 | 0.63 | 1.2:1 |

Compound A = Octhilinone
Compound B = Benzylbromoacetate
The synergistic ratios of compound A:compound B range from 40:1 to 1:40.
The preferred ratios are 10:1 to 1:5.

TABLE 7

Combination of Octhilinone and p-Chloro-m-xylenol

| Method of evaluation | end-point activity in ppm | | | | calculations | | | |
|---|---|---|---|---|---|---|---|---|
| | QA | QB | Qa | Qb | Qa/QA | Qb/QB | SI | Qa:Qb |
| *test against E. coli in M9G medium* | | | | | | | | |
| MIC | 125.0 | 250.0 | 8.0 | 125.0 | 0.06 | 0.50 | 0.56 | 1:15 |
| | 125.0 | 250.0 | 62.0 | 62.0 | 0.50 | 0.25 | 0.75 | 1:1 |
| MBCId | 250.0 | 250.0 | 8.0 | 125.0 | 0.03 | 0.50 | 0.53 | 1:15 |
| | 250.0 | 250.0 | 62.0 | 62.0 | 0.25 | 0.25 | 0.50 | 1:1 |
| MBC4d | 125.0 | 250.0 | 8.0 | 125.0 | 0.06 | 0.50 | 0.56 | 1:15 |
| | 125.0 | 250.0 | 62.0 | 62.0 | 0.50 | 0.25 | 0.75 | 1:1 |
| MBC7d | 125.0 | 250.0 | 8.0 | 125.0 | 0.06 | 0.50 | 0.56 | 1:15 |
| | 125.0 | 250.0 | 62.0 | 62.0 | 0.50 | 0.25 | 0.75 | 1:1 |
| *test against C. albicans in TSB medium* | | | | | | | | |
| MIC | 2.5 | 62.0 | 1.3 | 8.0 | 0.50 | 0.13 | 0.63 | 1:6.2 |
| *test against E. coli in TSB medium* | | | | | | | | |
| MIC | 125.0 | 125.0 | 62.0 | 31.0 | 0.50 | 0.25 | 0.75 | 2:1 |
| MBCId | 125.0 | 125.0 | 62.0 | 31.0 | 0.50 | 0.25 | 0.75 | 2:1 |

TABLE 7-continued

| | Combination of Octhilinone and p-Chloro-m-xylenol | | | | | | | |
|---|---|---|---|---|---|---|---|---|
| Method of | end-point activity in ppm | | | | calculations | | | |
| evaluation | QA | QB | Qa | Qb | Qa/QA | Qb/QB | SI | Qa:Qb |
| MBC2d | 125.0 | 125.0 | 62.0 | 31.0 | 0.50 | 0.25 | 0.75 | 2:1 |

Compound A = Octhilinone
Compound B = p-Chloro-m-xylenol
The synergistic ratios of compound A:compound B range from 2:1 to 1:15.
The preferred ratios are 2:1 to 1:15.

TABLE 8

| | Combination of Octhilinone and Bis-(2-hydroxy-5-chlorophenyl)sulfide | | | | | | | |
|---|---|---|---|---|---|---|---|---|
| Method of | end-point activity in ppm | | | | calculations | | | |
| evaluation | QA | QB | Qa | Qb | Qa/QA | Qb/QB | SI | Qa:Qb |
| | test against *E. coli* in M9G medium | | | | | | | |
| MIC | 125.0 | 125.0 | 62.0 | 31.0 | 0.50 | 0.25 | 0.75 | 2:1 |
| MBC4d | 125.0 | 125.0 | 62.0 | 62.0 | 0.50 | 0.50 | 1.00 | 1:1 |
| MBC7d | 125.0 | 125.0 | 62.0 | 62.0 | 0.50 | 0.50 | 1.00 | 1:1 |
| | test against *C. albicans* in TSB medium | | | | | | | |
| MIC | 0.3 | 31.0 | 0.1 | 8.0 | 0.26 | 0.26 | 0.52 | 1:100 |
| | 0.3 | 31.0 | 0.2 | 2.0 | 0.52 | 0.06 | 0.58 | 1:10 |
| MBCId | 0.6 | 31.0 | 0.1 | 8.0 | 0.13 | 0.26 | 0.39 | 1:100 |
| | 0.6 | 31.0 | 0.2 | 2.0 | 0.26 | 0.06 | 0.32 | 1:10 |
| MBC4d | 0.6 | 31.0 | 0.1 | 8.0 | 0.13 | 0.26 | 0.39 | 1:100 |
| | 0.6 | 31.0 | 0.2 | 2.0 | 0.26 | 0.06 | 0.32 | 1:10 |

Compound A = Octhilinone
Compound B = Bis-(2-hydroxy-5-chlorophenyl)sulfide
The synergistic ratios of compound A:compound B range from 2:1 to 1:100.
The preferred ratios are 2:1 to 1:10.

TABLE 9

| | Combination of Octhilinone and p-Tolyldiiodomethylsulfone | | | | | | | |
|---|---|---|---|---|---|---|---|---|

Compound A = Octhilinone
Compound B = p-Tolyldiiodomethylsulfone

| Method of | end-point activity in ppm | | | | Qa/ | Qb/ | | |
|---|---|---|---|---|---|---|---|---|
| evaluation | QA | QB | Qa | Qb | QA | QB | SI | Qa:Qb |
| | test against *E. coli* in TSB medium | | | | | | | |
| MIC | 250.0 | 100.0 | 2.0 | 50.0 | 0.01 | 0.50 | 0.51 | 1:25 |
| | 250.0 | 100.0 | 125.0 | 0.8 | 0.50 | 0.01 | 0.51 | 150:1 |
| MBC2d | 250.0 | 100.0 | 2.0 | 50.0 | 0.01 | 0.50 | 0.51 | 1:25 |
| | 250.0 | 100.0 | 125.0 | 0.8 | 0.50 | 0.01 | 0.51 | 150:1 |
| MBC6d | 250.0 | 100.0 | 2.0 | 50.0 | 0.01 | 0.05 | 0.51 | 1:25 |
| | 250.0 | 100.0 | 125.0 | 0.8 | 0.50 | 0.01 | 0.51 | 150:1 |
| | test against *C. albicans* in TSB medium | | | | | | | |
| MIC | 4.0 | 6.2 | 0.3 | 0.8 | 0.06 | 0.13 | 0.19 | 1:3.2 |
| | 4.0 | 6.2 | 0.5 | 0.4 | 0.13 | 0.06 | 0.19 | 1.2:1 |
| | 4.0 | 6.2 | 1.0 | 0.2 | 0.25 | 0.03 | 0.28 | 5:1 |
| MBC2d | 4.0 | 6.2 | 0.3 | 0.8 | 0.06 | 0.13 | 0.19 | 1:3.2 |
| | 4.0 | 6.2 | 0.5 | 0.4 | 0.13 | 0.06 | 0.19 | 1.2:1 |
| | 4.0 | 6.2 | 2.0 | 0.2 | 0.50 | 0.03 | 0.53 | 10:1 |
| MBC6d | 4.0 | 6.2 | 0.3 | 0.8 | 0.06 | 0.13 | 0.19 | 1:3.2 |
| | 4.0 | 6.2 | 0.5 | 0.4 | 0.13 | 0.06 | 0.19 | 1.2:1 |
| | 4.0 | 6.2 | 1.0 | 0.2 | 0.25 | 0.03 | 0.28 | 5:1 |
| | test against *E. coli* in M9G medium | | | | | | | |
| MBC2d | 125.0 | 25.0 | 62.0 | 6.2 | 0.50 | 0.25 | 0.75 | 10:1 |
| | 125.0 | 25.0 | 31.0 | 12.5 | 0.25 | 0.50 | 0.75 | 2.5:1 |
| | test against a mixed culture in TSB medium | | | | | | | |
| MIC | 250.0 | 50.0 | 31.0 | 12.5 | 0.12 | 0.25 | 0.37 | 2.5:1 |
| MBCId | 250.0 | 200.0 | 62.0 | 25.0 | 0.25 | 0.13 | 0.37 | 2.5:1 |
| MBC2d | 250.0 | 200.0 | 62.0 | 25.0 | 0.25 | 0.13 | 0.37 | 2.5:1 |
| MBC6d | 250.0 | 50.0 | 31.0 | 12.5 | 0.12 | 0.25 | 0.37 | 2.5:1 |

The synergistic ratios of compound A:compound B range from 150:1 to 1:25.
The preferred ratios are 2.5:1 to 1:25.

TABLE 10

| | Combination of Octhilinone and 3-Iodo-2-propynylbutylcarbamate | | | | | | | |
|---|---|---|---|---|---|---|---|---|

Compound A = Octhilinone
Compound B = 3-Iodo-2-propynylbutylcarbamate

| Method of | end-point activity in ppm | | | | Qa/ | Qb/ | | |
|---|---|---|---|---|---|---|---|---|
| evaluation | QA | QB | Qa | Qb | QA | QB | SI | Qa:Qb |
| | test against *E. coli* in TSB medium | | | | | | | |
| MIC | 250.0 | 200.0 | 125.0 | 100.0 | 0.50 | 0.50 | 1.00 | 1.2:1 |
| MBC2d | 250.0 | 200.0 | 125.0 | 100.0 | 0.50 | 0.50 | 1.00 | 1.2:1 |
| MBC6d | 250.0 | 200.0 | 125.0 | 100.0 | 0.50 | 0.50 | 1.00 | 1.2:1 |
| | test against *C. albicans* in TSB medium | | | | | | | |
| MIC | 2.0 | 6.2 | 0.3 | 1.6 | 0.13 | 0.26 | 0.38 | 1:6.2 |
| | 2.0 | 6.2 | 1.0 | 0.2 | 0.50 | 0.03 | 0.53 | 5:1 |
| MBC2d | 2.0 | 6.2 | 0.5 | 1.6 | 0.25 | 0.26 | 0.51 | 1:3.1 |
| | 2.0 | 6.2 | 1.0 | 0.2 | 0.50 | 0.03 | 0.53 | 5:1 |
| MBC6d | 2.0 | 6.2 | 0.5 | 1.6 | 0.25 | 0.26 | 0.51 | 1:3.1 |
| | 2.0 | 6.2 | 1.0 | 0.2 | 0.50 | 0.03 | 0.53 | 5:1 |
| | test against *E. coli* M9G medium | | | | | | | |
| M9G | 62.0 | 3.1 | 2.0 | 1.6 | 0.03 | 0.52 | 0.55 | 1.2:1 |
| MBC2d | 62.0 | 50.0 | 31.0 | 3.1 | 0.50 | 0.06 | 0.56 | 10:1 |
| | 62.0 | 50.0 | 2.0 | 25.0 | 0.03 | 0.50 | 0.53 | 1:12.5 |
| | test against a mixed-culture in TSB medium | | | | | | | |
| MIC | 250.0 | 200.0 | 31.0 | 100.0 | 0.12 | 0.50 | 0.62 | 1:3.1 |
| MBCId | 250.0 | 400.0 | 31.0 | 100.0 | 0.12 | 0.25 | 0.37 | 1:3.1 |
| MBC2d | 250.0 | 400.0 | 31.0 | 100.0 | 0.12 | 0.25 | 0.37 | 1:3.1 |
| MBC4d | 250.0 | 200.0 | 31.0 | 100.0 | 0.12 | 0.50 | 0.62 | 1:3.1 |

The synergistic ratios of compound A:compound B range from 10:1 to 1:12.5.
The preferred ratios are 5:1 to 1:3.1.

TABLE 11

| | Combination of Octhilinone and 5-Hydroxypoly(methyleneoxy)-methyl-1-aza-3,7-dioxabicyclo(3,3,0)octane | | | | | | | |
|---|---|---|---|---|---|---|---|---|

Compound A = Octhilinone
Compound B = 5-Hydroxypoly(methyleneoxy)-methyl-1-aza-3,7-dioxabicyclo(3,3,0)octane

| Method | end-point activity in ppm | | | | Qa/ | Qb/ | | |
|---|---|---|---|---|---|---|---|---|
| of evaluation | QA | QB | Qa | Qb | QA | QB | SI | Qa:Qb |
| | test against *E. coli* in TSB medium | | | | | | | |
| MIC | 125.0 | 250.0 | 62.0 | 125.0 | 0.50 | 0.50 | 1.00 | 1.2 |

TABLE 11-continued

Combination of Octhilinone and 5-Hydroxypoly(methyleneoxy)-methyl-1-aza-3,7-dioxabicyclo(3,3,0)octane Compound A = Octhilinone
Compound B = 5-Hydroxypoly(methyleneoxy)-methyl-1-aza-3,7-dioxabicyclo(3,3,0)octane

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| MBC2d | 125.0 | 500.0 | 31.0 | 250.0 | 0.25 | 0.50 | 0.75 | 1:8 |
| | 125.0 | 500.0 | 62.0 | 125.0 | 0.50 | 0.25 | 0.75 | 1:2 |
| MBC6d | 125.0 | 500.0 | 8.0 | 250.0 | 0.06 | 0.50 | 0.56 | 1:31 |
| | 125.0 | 500.0 | 62.0 | 125.0 | 0.50 | 0.25 | 0.75 | 1:2 |
| test against *C. albicans* in TSB medium | | | | | | | | |
| MIC | 2.0 | 1000.0 | 0.3 | 31.0 | 0.13 | 0.03 | 0.16 | 1:125 |
| | 2.0 | 1000.0 | 1.0 | 0.5 | 0.50 | 0.00 | 0.50 | 2:1 |
| MBC2d | 2.0 | 1000.0 | 0.3 | 31.0 | 0.13 | 0.03 | 0.16 | 1:125 |
| | 2.0 | 1000.0 | 1.0 | 4.0 | 0.50 | 0.00 | 0.50 | 1:4 |
| MBC6d | 2.0 | 1000.0 | 0.3 | 31.0 | 0.13 | 0.03 | 0.16 | 1:125 |
| | 2.0 | 1000.0 | 1.0 | 4.0 | 0.50 | 0.00 | 0.50 | 1:4 |
| test against *E. coli* M9G medium | | | | | | | | |
| MIC | 125.0 | 62.0 | 31.0 | 31.0 | 0.25 | 0.50 | 0.75 | 1:1 |
| MBC1d | 125.0 | 125.0 | 62.0 | 31.0 | 0.50 | 0.25 | 0.75 | 2:1 |
| | 125.0 | 125.0 | 16.0 | 62.0 | 0.13 | 0.50 | 0.62 | 1:4 |
| test against a mixed-culture in TSB medium | | | | | | | | |
| MIC | 250.0 | 500.0 | 31.0 | 125.0 | 0.12 | 0.25 | 0.37 | 1:4 |
| MBC1d | 250.0 | 1000.0 | 31.0 | 125.0 | 0.12 | 0.13 | 0.25 | 1:4 |
| MBC2d | 250.0 | 500.0 | 31.0 | 125.0 | 0.12 | 0.25 | 0.37 | 1:4 |
| MBC6d | 250.0 | 500.0 | 31.0 | 125.0 | 0.12 | 0.25 | 0.37 | 1:4 |

The synergistic ratios of compound A:compound B range from 2:1 to 1:125.
The preferred ratios are 1:4 to 1:31.

TABLE 12

Combination of Octhilinone and Dipropylamine ether

Compound A = Octhilinone
Compound B = Dipropylamine ether

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium | | | | | | | | |
| MIC | 125.0 | 31.0 | 2.0 | 16.0 | 0.02 | 0.52 | 0.53 | 1:8 |
| | 125.0 | 31.0 | 8.0 | 8.0 | 0.06 | 0.26 | 0.32 | 1:1 |
| | 125.0 | 31.0 | 62.0 | 2.0 | 0.50 | 0.06 | 0.56 | 31:1 |
| MBC1d | 250.0 | 62.0 | 62.0 | 8.0 | 0.25 | 0.13 | 0.38 | 8:1 |
| | 250.0 | 62.0 | 2.0 | 31.0 | 0.01 | 0.50 | 0.51 | 1:16 |
| MBC4d | 125.0 | 31.0 | 16.0 | 16.0 | 0.13 | 0.52 | 0.64 | 1:1 |
| | 125.0 | 31.0 | 62.0 | 2.0 | 0.50 | 0.06 | 0.56 | 31:1 |
| MBC7d | 125.0 | 31.0 | 2.0 | 16.0 | 0.02 | 0.52 | 0.53 | 1:8 |
| | 125.0 | 31.0 | 62.0 | 2.0 | 0.50 | 0.06 | 0.56 | 31:1 |
| test against *C. albicans* in TSB medium | | | | | | | | |
| MIC | 1.3 | 125.0 | 0.6 | 16.0 | 0.50 | 0.13 | 0.62 | 1:25 |
| test against *E. coli* in TSB medium | | | | | | | | |
| MIC | 125.0 | 50.0 | 31.0 | 6.2 | 0.25 | 0.12 | 0.37 | 5:1 |
| | 125.0 | 50.0 | 8.0 | 12.5 | 0.06 | 0.25 | 0.31 | 1:1.6 |
| MBC1d | 125.0 | 50.0 | 31.0 | 6.2 | 0.25 | 0.12 | 0.37 | 5:1 |
| | 125.0 | 50.0 | 16.0 | 12.5 | 0.13 | 0.25 | 0.38 | 1.3:1 |
| MBC2d | 125.0 | 50.0 | 31.0 | 6.2 | 0.25 | 0.12 | 0.37 | 5:1 |
| | 125.0 | 50.0 | 16.0 | 12.5 | 0.13 | 0.25 | 0.38 | 1.3:1 |
| test against a mixed-culture in TSB medium | | | | | | | | |
| MIC | 250.0 | 500.0 | 31.0 | 50.0 | 0.12 | 0.10 | 0.22 | 1:1.6 |
| | 250.0 | 500.0 | 62.0 | 25.0 | 0.25 | 0.05 | 0.30 | 2.5:1 |
| MBC6d | 250.0 | 500.0 | 62.0 | 25.0 | 0.25 | 0.05 | 0.30 | 2.5:1 |

The synergistic ratios of compound A:compound B range from 8:1 to 1:25.
The preferred ratios are 2.5:1 to 1:6.

TABLE 13

Combination of Octhilinone and Dodecylamine

Compound A = Octhilinone
Compound B = Dodecylamine

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against a mixed-culture in TSB medium | | | | | | | | |
| MIC | 250.0 | 100.0 | 31.0 | 25.0 | 0.12 | 0.25 | 0.37 | 1.2:1 |
| MBC1d | 250.0 | 200.0 | 31.0 | 25.0 | 0.12 | 0.13 | 0.25 | 1.2:1 |
| MBC2d | 250.0 | 100.0 | 31.0 | 25.0 | 0.12 | 0.25 | 0.37 | 1.2:1 |
| MBC6d | 250.0 | 100.0 | 31.0 | 25.0 | 0.12 | 0.25 | 0.37 | 1.2:1 |
| test against *E. coli* in M9G medium | | | | | | | | |
| MIC | 125.0 | 25.0 | 62.0 | 6.2 | 0.50 | 0.25 | 0.75 | 10:1 |
| | 125.0 | 25.0 | 31.0 | 12.5 | 0.25 | 0.50 | 0.75 | 2.5:1 |
| MBC1d | 125.0 | 25.0 | 31.0 | 12.5 | 0.25 | 0.50 | 0.75 | 2.5:1 |
| MBC2d | 125.0 | 25.0 | 31.0 | 12.5 | 0.25 | 0.50 | 0.75 | 2.5:1 |
| | 125.0 | 25.0 | 62.0 | 6.2 | 0.50 | 0.25 | 0.75 | 10:1 |

The synergistic ratios of compound A:compound B range from 10:1 to 1.2:1.
The preferred ratios are 2.5:1 to 1.2:1.

TABLE 14

Combination of Octhilinone and N-(hydroxymethyl)-N'-(1,3-di(hydroxymethyl)-2,5-dioxo-4-imidazolidinyl)-N'-(hydroxymethyl)urea Compound A = Octhilinone
Compound B = N-(hydroxymethyl)-N'-(1,3-di(hydroxymethyl)-2,5-dioxo-4-imidazolidinyl-N'-(hydroxymethyl)urea

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against a mixed-culture in TSB medium | | | | | | | | |
| MIC | 250.0 | 500.0 | 31.0 | 250.0 | 0.12 | 0.50 | 0.62 | 1:8 |
| MBC1d | 250.0 | 1000.0 | 62.0 | 500.0 | 0.25 | 0.50 | 0.75 | 1:8 |
| MBC2d | 250.0 | 1000.0 | 31.0 | 250.0 | 0.12 | 0.25 | 0.37 | 1:8 |
| MBC6d | 250.0 | 1000.0 | 31.0 | 250.0 | 0.12 | 0.25 | 0.37 | 1:8 |
| test against *E. coli* in M9G medium | | | | | | | | |
| MIC | 125.0 | 125.0 | 31.0 | 62.0 | 0.25 | 0.50 | 0.75 | 1:2 |
| MBC1d | 250.0 | 500.0 | 16.0 | 125.0 | 0.06 | 0.25 | 0.31 | 1:8 |
| | 250.0 | 500.0 | 31.0 | 62.0 | 0.12 | 0.12 | 0.25 | 1:2 |
| | 250.0 | 500.0 | 62.0 | 31.0 | 0.25 | 0.06 | 0.31 | 2:1 |
| MBC4d | 125.0 | 125.0 | 31.0 | 62.0 | 0.25 | 0.50 | 0.75 | 1:2 |
| MBC7d | 125.0 | 125.0 | 31.0 | 62.0 | 0.25 | 0.50 | 0.75 | 1:2 |
| test against *E. coli* in TSB medium | | | | | | | | |
| MIC | 125.0 | 500.0 | 62.0 | 250.0 | 0.50 | 0.50 | 1.00 | 1:4 |
| MBC2d | 125.0 | 1000.0 | 31.0 | 500.0 | 0.25 | 0.50 | 0.75 | 1:16 |
| | 125.0 | 1000.0 | 62.0 | 250.0 | 0.50 | 0.25 | 0.75 | 1:4 |
| MBC6d | 125.0 | 1000.0 | 8.0 | 500.0 | 0.06 | 0.50 | 0.56 | 1:62 |
| | 125.0 | 1000.0 | 62.0 | 250.0 | 0.50 | 0.25 | 0.75 | 1:4 |

The synergistic ratios of compound A:compound B range from 2:1 to 1:62.
The preferred ratios are 1:2 to 1:8.

TABLE 15

Combination of Octhilinone and 1-(3-Chloroallyl)-3,5,7-triaza-1-azoniaadamantane chloride Compound A = Octhilinone
Compound B = 1-(3-Chloroallyl)-3,5,7-triaza-1-azoniaadamantane chloride

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium | | | | | | | | |
| MIC | 125.0 | 125.0 | 16.0 | 62.0 | 0.13 | 0.50 | 0.62 | 1:4 |
| | 125.0 | 125.0 | 62.0 | 31.0 | 0.50 | 0.25 | 0.74 | 2:1 |
| MBC1d | 250.0 | 1000.0 | 62.0 | 125.0 | 0.25 | 0.13 | 0.37 | 1:2 |
| | 250.0 | 1000.0 | 31.0 | 250.0 | 0.12 | 0.25 | 0.37 | 1:8 |
| | 250.0 | 1000.0 | 8.0 | 500.0 | 0.03 | 0.50 | 0.53 | 1:62.5 |
| MBC4d | 125.0 | 125.0 | 16.0 | 62.0 | 0.13 | 0.50 | 0.62 | 1:4 |
| | 125.0 | 125.0 | 62.0 | 31.0 | 0.50 | 0.25 | 0.74 | 2:1 |
| MBC7d | 125.0 | 125.0 | 16.0 | 62.0 | 0.13 | 0.50 | 0.62 | 1:4 |
| | 125.0 | 125.0 | 62.0 | 31.0 | 0.50 | 0.25 | 0.74 | 2:1 |

The synergistic ratios of compound A:compound B range from 2:1 to 1:62.5.
The preferred ratios are 2:1 to 1:4.

TABLE 16

Combination of Octhilinone and 1,2-Dibromo-2,4-dicyanobutane

Compound A = Octhilinone
Compound B = 1,2-Dibromo-2,4-dicyanobutane

| Method of eval-uation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in TSB medium ||||||||  |
| MIC | 125.0 | 250.0 | 31.0 | 50.0 | 0.25 | 0.20 | 0.45 | 1:1.6 |
| MBC2d | 125.0 | 250.0 | 62.0 | 50.0 | 0.50 | 0.20 | 0.70 | 1.2:1 |
| MBC6d | 125.0 | 250.0 | 62.0 | 50.0 | 0.50 | 0.20 | 0.70 | 1.2:1 |
| test against *C. albicans* in TSB medium ||||||||  |
| MIC | 2.5 | 62.0 | 1.3 | 4.0 | 0.50 | 0.06 | 0.56 | 1:3.2 |
|  | 2.5 | 62.0 | 0.6 | 16.0 | 0.25 | 0.26 | 0.51 | 1:25 |
| test against *E. coli* in M9G medium ||||||||  |
| MIC | 62.0 | 25.0 | 31.0 | 3.1 | 0.50 | 0.12 | 0.62 | 10:1 |
|  | 62.0 | 25.0 | 8.0 | 6.2 | 0.13 | 0.25 | 0.38 | 1.2:1 |
|  | 62.0 | 25.0 | 4.0 | 12.5 | 0.06 | 0.50 | 0.56 | 1:3.2 |
| MBC1d | 62.0 | 100.0 | 31.0 | 3.1 | 0.50 | 0.03 | 0.53 | 1:1.6 |
|  | 62.0 | 100.0 | 8.0 | 12.5 | 0.13 | 0.13 | 0.25 | 1:1.6 |
|  | 62.0 | 100.0 | 4.0 | 50.0 | 0.06 | 0.50 | 0.56 | 1:12.5 |
| test against a mixed-culture in TSB medium ||||||||  |
| MIC | 250.0 | 50.0 | 16.0 | 25.0 | 0.06 | 0.50 | 0.56 | 1:1.6 |
| MBC1d | 250.0 | 400.0 | 62.0 | 50.0 | 0.25 | 0.13 | 0.37 | 1.2:1 |
| MBC2d | 250.0 | 200.0 | 31.0 | 50.0 | 0.12 | 0.25 | 0.37 | 1:1.6 |
| MBC6d | 250.0 | 200.0 | 16.0 | 25.0 | 0.06 | 0.13 | 0.19 | 1:1.6 |

The synergistic ratios of compound A:compound B range from 10:1 to 1:25.
The preferred ratios are 1.2:1 to 1:3.2.

TABLE 17

Combination of Octhilinone and N,N-dimethyl-N'-phenyl-N'-(fluorodichloromethylthio)sulfamide Compound A = Octhilinone
Compound B = N,N-dimethyl-N'-phenyl-N'-(fluorodichloromethylthio)sulfamide

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium ||||||||  |
| MIC | 125.0 | 500.0 | 62.0 | 62.0 | 0.50 | 0.12 | 0.62 | 1:1 |
|  | 125.0 | 500.0 | 31.0 | 125.0 | 0.25 | 0.25 | 0.50 | 1:4 |
| MBC1d | 125.0 | 500.0 | 62.0 | 62.0 | 0.50 | 0.12 | 0.62 | 1:1 |
| test against *C. albicans* in TSB medium ||||||||  |
| MIC | 2.5 | 500.0 | 1.3 | 125.0 | 0.50 | 0.25 | 0.75 | 1:100 |

The synergistic ratios of compound A:compound B range from 1:1 to 1:100.
The preferred ratios are 1:1 to 1:4.

TABLE 18

Combination of Octhilinone and N,N'-di(hydroxymethyl)-5,5'-dimethylhydantoin

Compound A = Octhilinone
Compound B = N,N'-di(hydroxymethyl)-5,5'-dimethylhydantoin

| Method of evalu-ation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium ||||||||  |
| MIC | 125.0 | 250.0 | 8.0 | 125.0 | 0.06 | 0.50 | 0.56 | 1:15 |
| MBC1d | 125.0 | 250.0 | 8.0 | 125.0 | 0.06 | 0.50 | 0.56 | 1:15 |
| test against mixed-culture in TSB medium ||||||||  |
| MIC | 250.0 | 2000.0 | 62.0 | 500.0 | 0.25 | 0.25 | 0.50 | 1:8 |
| MBC1d | 250.0 | 2000.0 | 62.0 | 500.0 | 0.25 | 0.25 | 0.50 | 1:8 |
| MBC2d | 250.0 | 2000.0 | 62.0 | 500.0 | 0.25 | 0.25 | 0.50 | 1:8 |
| MBC6d | 250.0 | 2000.0 | 62.0 | 500.0 | 0.25 | 0.25 | 0.50 | 1:8 |

The synergistic ratios of compound A:compound B range from 1:8 to 1:15.
The preferred ratios are 1:8 to 1:15.

TABLE 19

Combination of Octhilinone and 2-Bromo-2-nitropropanediol

Compound A = Octhilinone
Compound B = 2-Bromo-2-nitropropanediol

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium ||||||||  |
| MBC1d | 125.0 | 8.0 | 16.0 | 4.0 | 0.13 | 0.50 | 0.63 | 4:1 |
| test against *C. albicans* in TSB medium ||||||||  |
| MIC | 2.5 | 62.0 | 0.1 | 31.0 | 0.03 | 0.50 | 0.53 | 1:400 |
|  | 2.5 | 62.0 | 0.6 | 16.0 | 0.25 | 0.26 | 0.51 | 1:25 |
|  | 2.5 | 62.0 | 1.3 | 5.0 | 0.50 | 0.08 | 0.58 | 1:4 |
| test against a mixed-culture in TSB medium ||||||||  |
| MIC | 250.0 | 4.0 | 4.0 | 2.0 | 0.02 | 0.50 | 0.52 | 2:1 |
| MBC1d | 250.0 | 32.0 | 16.0 | 8.0 | 0.06 | 0.25 | 0.31 | 2:1 |
| MBC2d | 250.0 | 16.0 | 8.0 | 4.0 | 0.03 | 0.25 | 0.28 | 2:1 |
| MBC6d | 250.0 | 8.0 | 4.0 | 2.0 | 0.02 | 0.25 | 0.27 | 2:1 |

The synergistic ratios of compound A:compound B range from 4:1 to 1:400.
The preferred ratios are 4:1 to 1:4.

TABLE 20

Combination of Octhilinone and Methylene-bis-thiocyanate

Compound A = Octhilinone
Compound B = Methylene-bis-thiocyanate

| Method of evaluation | end point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium ||||||||  |
| MIC | 125.0 | 4.0 | 16.0 | 2.0 | 0.13 | 0.50 | 0.63 | 8:1 |
|  | 125.0 | 4.0 | 62.0 | 1.0 | 0.50 | 0.25 | 0.75 | 62:1 |
| MBC1d | 250.0 | 31.0 | 62.0 | 16.0 | 0.25 | 0.52 | 0.77 | 4:1 |
|  | 250.0 | 31.0 | 125.0 | 4.0 | 0.50 | 0.13 | 0.63 | 31:1 |
| MBC4d | 125.0 | 4.0 | 31.0 | 2.0 | 0.25 | 0.50 | 0.75 | 16:1 |
| MBC7d | 125.0 | 4.0 | 31.0 | 2.0 | 0.25 | 0.50 | 0.75 | 16:1 |
|  | 125.0 | 4.0 | 62.0 | 1.0 | 0.50 | 0.25 | 0.75 | 62:1 |
| test against *C. albicans* in TSB medium ||||||||  |
| MIC | 2.5 | 6.2 | 0.2 | 3.1 | 0.06 | 0.50 | 0.56 | 1:20 |
|  | 2.5 | 6.2 | 0.6 | 1.6 | 0.25 | 0.26 | 0.51 | 1:2.5 |
|  | 2.5 | 6.2 | 1.3 | 0.8 | 0.50 | 0.13 | 0.63 | 1.6:1 |
| test against a mixed-culture in TSB medium ||||||||  |
| MBC1d | 250.0 | 100.0 | 25.0 | 50.0 | 0.10 | 0.50 | 0.60 | 1:2 |
| MBC2d | 250.0 | 100.0 | 25.0 | 50.0 | 0.10 | 0.50 | 0.60 | 1:2 |
| MBC6d | 250.0 | 12.5 | 3.1 | 6.2 | 0.01 | 0.50 | 0.51 | 1:2 |

The synergistic ratios of compound A:compound B range from 62:1 to 1:20.
The preferred ratios are 16:1 to 1:2.

TABLE 21

Combination of Octhilinone and 2,4-Dichlorobenzyl alcohol

Compound A = Octhilinone
Compound B = 2,4-Dichlorobenzyl alcohol

| Method of evaluation | end-point activity in ppm | | | | Qa/QA | Qb/QB | SI | Qa:Qb |
|---|---|---|---|---|---|---|---|---|
| | QA | QB | Qa | Qb | | | | |
| test against *E. coli* in M9G medium ||||||||  |
| MIC | 125.0 | 62.0 | 62.0 | 16.0 | 0.50 | 0.26 | 0.75 | 4:1 |
| MBC1d | 250.0 | 125.0 | 31.0 | 62.0 | 0.12 | 0.50 | 0.62 | 1:2 |
|  | 250.0 | 125.0 | 62.0 | 31.0 | 0.25 | 0.25 | 0.50 | 2:1 |
| MBC4d | 125.0 | 125.0 | 31.0 | 62.0 | 0.25 | 0.50 | 0.75 | 1:2 |
|  | 125.0 | 125.0 | 62.0 | 31.0 | 0.50 | 0.25 | 0.75 | 2:1 |
| MBC7d | 125.0 | 125.0 | 31.0 | 62.0 | 0.25 | 0.50 | 0.75 | 1:2 |
|  | 125.0 | 125.0 | 62.0 | 16.0 | 0.50 | 0.13 | 0.62 | 4:1 |
| test against *C. albicans* in TSB medium ||||||||  |
| MIC | 2.5 | 125.0 | 1.3 | 8.0 | 0.50 | 0.06 | 0.56 | 1:6.2 |

The synergistic ratios of compound A:compound B range from 4:1 to 1:6.2.
The preferred ratios are 4:1 to 1:2.

TABLE 22

Combination of Octhilinone Sodium dichlorophene

Compound A = Octhilinone
Compound B = Sodium dichlorophene

| Method of evaluation | end-point activity in ppm | | | | calculations | | |
|---|---|---|---|---|---|---|---|
| | QA | QB | Qa | Qb | Qa/QA | Qb/QB | SI |
| test against *E. coli* in M9G medium | | | | | | | |
| MIC | 125.0 | 16.0 | 125.0 | 16.0 | NA | NA | NA |
| MBC1d | 250.0 | 16.0 | 250.0 | 16.0 | NA | NA | NA |
| MBC4d | 125.0 | 16.0 | 125.0 | 16.0 | NA | NA | NA |
| MBC7d | 125.0 | 16.0 | 125.0 | 16.0 | NA | NA | NA |
| test against *E. coli* in TSB medium | | | | | | | |
| MIC | 125.0 | 62.0 | 125.0 | 62.0 | NA | NA | NA |
| MBC1d | 125.0 | 62.0 | 125.0 | 62.0 | NA | NA | NA |
| test against *C. albicans* in TSB medium | | | | | | | |
| MIC | 2.5 | 50.0 | 1.3 | 25.0 | 0.50 | 0.50 | 1.00 |

NA = not applicable because it is not end-point of activity.

As can be seen by review of Tables 1-21, the compositions demonstrate synergistic antimicrobial activities as measured by minimum inhibitory concentrations (MIC) and synergistic biocidal activity as measured by minimum biocidal concentrations (MBC), and show surprisingly greater activity than the algebraic sum of the individual ingredients which make up the respective composition.

In contrast, an example of non-synergistic combination of octhilinone and sodium dichlorophene is in Table 22. In this example of non-synergism, the antibacterial activities of either octhilinone or sodium dichlorophene as measured by the activities against *E. coli* are not affected by the presence or the absence of the other component in the combination. It is also not antagonistic because no loss of activity of either component in the combination was detected. The antifungal activity, as measured by activity against *C. albicans*, indeed increased as a result of the combination. The increased activity, however, is merely additive because the synergy index is 1.

The synergistic activities in most cases are applicable to bacteria, fungi, and a mixture of bacteria and fungi. Thus, the combinations not only lower the use-level of biocide but also broaden the spectrum of activity. This is especially useful in situations where either component alone does not achieve the best results due to weak activity against certain organisms. For octhilinone combinations, the synergistic activity against Gram-negative bacteria is most significant in situations where both bacteria and fungi are present in the system.

Another example is provided below to demonstrate the advantage of using octhilinone-containing compositions. In this example, a combination of octhilinone and 5-hydroxypoly(methyleneoxy)-methyl-1-aza-3,7-dioxabicyclo(3,3,0)octane (DBO) was evaluated for the control of fouling bacteria and fungi in a metalworking fluid. The test was a 4-week multiple challenge efficacy test. Octhilinone, DBO, and the combination of octhilinone and DBO were added to specified concentrations into 50 ml use dilution of the metalworking fluid in 4 oz. jars. Each jar was then inoculated weekly with a mixed culture of bacteria and fungi isolated from naturally contaminated metalworking fluid to make final concentration of about $2 \times 10^6$ fungi and $2 \times 10^7$ bacteria per ml of fluid. The viable counts were determined 7 days after each inoculation by 10-fold serial dilutions and platings on Trypicase Soy Agar (Difco) for bacteria and on Rose Bengal Agar with 100 ppm chloramphenicol (Oxoid) for fungi. Results of such tests are shown in Table 23. Rating of efficacy is based on generally accepted criteria in the metalworking fluid industry that $>10^5$ bacteria or $10^3$ fungi per ml failed the efficacy test, and less than $10^5$ bacteria and $10^3$ fungi passed the test. When a biocide passes all 4 weekly challenge tests, it will effectively preserve the metalworking fluid. It is evident after examining Table 24 that a mixture of octhilinone and DBO preferably at ratios from 1:4 to 1:31, provides a strong synergism and effective control of bacteria, fungi, and the mixed culture of bacteria and fungi. In fact, either octhilinone or DBO is not used as a general biocide in preserving metalworking fluid due to high dosage requirement and thereby cost disadvantage. Now, with the synergistic combination of octhilinone and DBO they can be used effectively as a general biocide for preserving metalworking fluids.

TABLE 23

Efficacy Test on Combinations of Octhilinone and DBO in a Metalworking Fluid

| Sample Nos. | Treatment | | Efficacy* | | | |
|---|---|---|---|---|---|---|
| | Octhilinone ppm a.i. | DBO ppm a.i. | 1 Wk. | 2 Wks. | 3 Wks. | 4 Wks. |
| 1 | 0 | 0 | 4 | 4 | 4 | 4 |
| 2 | 0 | 125 | 2 | 2 | 4 | 4 |
| 3 | 0 | 250 | 2 | 2 | 4 | 4 |
| 4 | 0 | 500 | 2 | 2 | 2 | 4 |
| 5 | 0 | 750 | 0 | 2 | 2 | 4 |
| 6 | 0 | 1000 | 0 | 0 | 0 | 2 |
| 7 | 0 | 1250 | 0 | 0 | 0 | 0 |
| 8 | 4 | 0 | 3 | 4 | 4 | 4 |
| 9 | 8 | 0 | 3 | 3 | 3 | 4 |
| 10 | 16 | 0 | 3 | 3 | 3 | 4 |
| 11 | 32 | 0 | 3 | 3 | 3 | 3 |
| 12 | 64 | 0 | 3 | 3 | 3 | 3 |
| 13 | 4 | 250 | 0 | 0 | 2 | 4 |
| 14 | 8 | 250 | 0 | 0 | 0 | 0 |
| 15 | 16 | 250 | 0 | 0 | 0 | 0 |
| 16 | 32 | 250 | 0 | 0 | 0 | 0 |
| 17 | 64 | 250 | 0 | 0 | 0 | 0 |
| 18 | 4 | 500 | 0 | 0 | 2 | 2 |
| 19 | 8 | 500 | 0 | 0 | 0 | 0 |
| 20 | 16 | 500 | 0 | 0 | 0 | 0 |
| 21 | 32 | 500 | 0 | 0 | 0 | 0 |
| 22 | 64 | 500 | 0 | 0 | 0 | 0 |
| 23 | 4 | 750 | 0 | 0 | 0 | 0 |
| 24 | 8 | 750 | 0 | 0 | 0 | 0 |
| 25 | 16 | 750 | 0 | 0 | 0 | 0 |
| 26 | 32 | 750 | 0 | 0 | 0 | 0 |
| 27 | 64 | 750 | 0 | 0 | 0 | 0 |

*4 = failed both bacteria ($>10^5$ cfu/ml) and fungi ($>10^3$ cfu/ml)
3 = failed bacteria only
2 = failed fungi only
0 = passed both bacteria ($<10^5$ cfu/ml) and fungi ($<10^3$ cfu/ml)

TABLE 24

Calculations for Synergy Index (SI) of Octhilinone (A) and DBO (B) Combinations

| Sample Nos. | Ratio (a):(b) | SI for Bacteria* | SI for Fungi | SI for Mixed Culture* |
|---|---|---|---|---|
| 14 | 1:31 | 250/1000 + 8/500 = 0.26 | 250/1250 + 8/32 = 0.45 | 250/1250 + 8/500 = 0.21 |
| 15 | 1:15 | 250/1000 + 16/500 = 0.28 | 250/1250 + 16/32 = 0.70 | 250/1250 + 16/500 = 0.23 |
| 16 | 1:8 | 250/1000 + 32/500 = 0.31 | NA** | 250/2250 + 32/500 = 0.26 |
| 17 | 1:4 | 250/1000 + 64/500 = 0.37 | NA | 250/1250 + 64/500 = 0.32 |
| 18 | 1:125 | 500/1000 + 4/500 = 0.50 | NA | NA |
| 19 | 1:62 | 500/1000 + 8/500 = 0.51 | 500/1250 + 8/500 = 0.65 | 500/1250 + 8/500 = 0.41 |

TABLE 24-continued

| | | Calculations for Synergy Index (SI) of Octhilinone (A) and DBO (B) Combinations | | |
|---|---|---|---|---|
| Sample Nos. | Ratio (a):(b) | SI for Bacteria* | SI for Fungi | SI for Mixed Culture* |
| 20 | 1:31 | 500/1000 + 16/500 = 0.53 | 500/1250 + 16/32 = 0.90 | 500/1250 + 16/500 = 0.43 |
| 21 | 1:16 | 500/1000 + 32/500 = 0.56 | NA | 500/1250 + 32/500 = 0.46 |
| 22 | 1:8 | 500/1000 + 64/500 = 0.62 | NA | 500/1250 + 64/500 = 0.52 |
| 23 | 1:187 | 750/1000 + 4/500 = 0.75 | 750/1250 + 4/32 = 0.88 | 750/1250 + 4/500 = 0.60 |
| 24 | 1:94 | 750/1000 + 8/500 = 0.76 | NA | 750/1250 + 8/500 = 0.61 |
| 25 | 1:47 | 750/1000 + 16/500 = 0.78 | NA | 750/1250 + 16/500 = 0.63 |
| 26 | 1:23 | 750/1000 + 32/500 = 0.81 | NA | 750/1250 + 32/500 = 0.66 |
| 27 | 1:12 | 750/1000 + 64/500 = 0.87 | NA | 750/1250 + 64/500 = 0.72 |

*The end-point activity of Octhilinone against bacteria and the mixed culture was independently determined to be 500 ppm.
**NA = Not applicable because they are not end points

What is claimed is:

1. A microbicidal composition comprising a synergistic mixture the first component of which is 2-n-octyl-4-isothiazolin-3-one and the second component of which is N,N-di(hydroxymethyl)-5,5'-dimethylhydantoin; wherein the ratio of first component to second component is in the range of from about 1:8 to about 1:15.

2. A method for inhibiting the growth of a member selected from the group consisting of bacteria, fungi, algae and mixtures thereof in a locus subject to contamination by said member, which comprises incorporating onto or into the locus, in an amount which is effective to adversely affect the growth of said member, the composition of claim 1.

3. The method of claim 2 wherein the locus is an aqueous medium.

4. The method of claim 3 wherein the composition is between from about 20 to about 400 ppm.

5. The method of claim 3 wherein the composition is between from about 25 to about 200 ppm.

* * * * *